United States Patent
Hundertmark et al.

(10) Patent No.: US 9,446,182 B2
(45) Date of Patent: Sep. 20, 2016

(54) FILLING DEVICE OF A FLUID SYSTEM

(71) Applicant: B. BRAUN AVITUM AG, Melsungen (DE)

(72) Inventors: Charleen Hundertmark, Kassel (DE); Judith Hieronymi, Gudensberg (DE); Michele Susca, Dossenheim (DE); Anne-Marie Mihailescu, Melsungen (DE); Claudia Freitag, Gudensberg (DE); Rainer Hector, Osnabrueck (DE)

(73) Assignee: B. Braun Aviitum AG, Melsungen (DE)

( * ) Notice: Subject to any disclaimer, the term of this patent is extended or adjusted under 35 U.S.C. 154(b) by 0 days.

(21) Appl. No.: 14/784,791

(22) PCT Filed: Apr. 16, 2014

(86) PCT No.: PCT/EP2014/057748
§ 371 (c)(1),
(2) Date: Oct. 15, 2015

(87) PCT Pub. No.: WO2014/170381
PCT Pub. Date: Oct. 23, 2014

(65) Prior Publication Data
US 2016/0058935 A1    Mar. 3, 2016

(30) Foreign Application Priority Data

Apr. 19, 2013  (DE) .................... 20 2013 101 695 U
Jan. 13, 2014  (DE) ....................... 10 2014 100 324

(51) Int. Cl.
*A61J 1/20*      (2006.01)
*A61M 1/16*      (2006.01)
(Continued)

(52) U.S. Cl.
CPC ............. *A61M 1/1668* (2014.02); *A61J 1/201* (2015.05); *A61J 1/2048* (2015.05); *A61J 1/22* (2013.01);
(Continued)

(58) Field of Classification Search
CPC ........ A61J 1/201; A61J 1/22; A61M 1/3643; A61M 1/3647; A61M 39/223
See application file for complete search history.

(56) References Cited

U.S. PATENT DOCUMENTS 4,819,653 A   4/1989  Marks
4,844,810 A   7/1989  Richalley et al.
(Continued)

FOREIGN PATENT DOCUMENTS

| CA | 2 528 721 | 12/2004 |
|---|---|---|
| CN | 1809393 | 7/2006 |
| DE | 10 2009 004 461 | 7/2010 |

OTHER PUBLICATIONS

Chinese Office Action with Search Report for CN 201480022293.1, with translation, dated May 26, 2016.
(Continued)

*Primary Examiner* — Philip R Wiest
*Assistant Examiner* — Kai Weng
(74) *Attorney, Agent, or Firm* — RatnerPrestia

(57) ABSTRACT

A filling device of a fluid conducting system of an extracorporeal blood treatment device is disclosed. The filling device includes a spike that is adapted for connection to a single fluid connector of a medical fluid container of the fluid system and a manually operable fluid blocking mechanism that is arranged directly downstream of the spike and is adapted or provided in such a way so as to remain fluidly connected with the spike while the filling device is in operation. The fluid blocking mechanism has at least one fluid outlet connector that is adapted so that a line section or hose of the fluid conducting system, preferably an arterial line section of a blood purification device, can be connected to it in a detachable manner while the filling device is in operation.

9 Claims, 2 Drawing Sheets

(51) Int. Cl.
  *A61M 39/22* (2006.01)
  *A61M 1/36* (2006.01)
  *F16K 11/072* (2006.01)
  *F16K 31/60* (2006.01)
  *A61J 1/22* (2006.01)

(52) U.S. Cl.
  CPC ............ *A61M 1/367* (2013.01); *A61M 1/3643* (2013.01); *A61M 1/3647* (2014.02); *A61M 39/223* (2013.01); *F16K 11/072* (2013.01); *F16K 31/60* (2013.01)

(56) References Cited

U.S. PATENT DOCUMENTS

| | | | |
|---|---|---|---|
| 5,259,961 A * | 11/1993 | Eigendorf | A61M 1/3643 210/646 |
| 5,334,163 A | 8/1994 | Sinnett | |
| 5,334,315 A | 8/1994 | Matkovich et al. | |
| 5,647,845 A | 7/1997 | Haber et al. | |
| 6,221,041 B1 | 4/2001 | Russo | |
| 2002/0079258 A1 | 6/2002 | Sawa | |
| 2004/0002684 A1 | 1/2004 | Lopez | |
| 2005/0113766 A1 | 5/2005 | Mottola et al. | |
| 2008/0214981 A1 | 9/2008 | Delnevo et al. | |
| 2009/0076433 A1 * | 3/2009 | Folden | A61M 1/3643 604/4.01 |

OTHER PUBLICATIONS

International Search Report for WO 2014/170381 dated Jul. 31, 2014.
German Search Report for DE 10 2014 100 324.1 dated Mar. 3, 2014.

* cited by examiner

FILLING DEVICE OF A FLUID SYSTEM

CROSS REFERENCE TO RELATED APPLICATIONS

This application is the U.S. national phase application of PCT International Application No. PCT/EP2014/057748 filed Apr. 16, 2014, which claims priority to German Patent Application No. DE 20 2013 101 695.0 filed Apr. 19, 2013, and German Patent Application No. DE 10 2014 100 324.1 filed Jan. 13, 2014, the contents of each application being incorporated by reference herein.

FIELD OF THE INVENTION

The invention in hand concerns the filling device of a fluid conducting system and/or liquid system, in particular an extracorporeal blood treatment device, for example a dialysis or apheresis machine.

BACKGROUND OF THE INVENTION

The hydraulic system (blood-side fluid system) of a blood treatment device, for example a dialysis machine, has to be filled with fluid, for example an NaCl solution or another sterile physiological solution, before being connected up to a patient, in such a way that air pockets in the system that would be dangerous for a patient connected up to the fluids of the system are eliminated. Furthermore, the hydraulic system can be flushed with the filled-in fluid for a certain period of time in order to filter/wash out any contaminants, dirt particles, etc. that may have deposited in the system before the system is connected up to the patient. On an extracorporeal blood treatment device, these two procedures are performed in the scope of a filling-circulation cycle.

In the state of the art, there are fluid containers, preferably in the shape of plastic bags, that are specially designed for extracorporeal blood treatment devices of this relevant type in order to enable, among others, the device functions as defined above. This kind of fluid containers is also manufactured and sold by the applicant filing the application in hand.

As a rule, such a fluid container has a fluid intake chamber and two preferably closable fluid connectors. On a first of the two connectors, an arterial line section, and on the second connector, a venous line section of the hydraulic system (fluid system or also referred to as fluid conducting system) of the extracorporeal blood treatment device can be connected. The fluid bag as well as the two line sections together constitute a circulation device of the extracorporeal blood treatment device.

For the fluid system filling process, first the arterial line section is connected to the first fluid connector of the bag, and after opening of the first fluid connector, the hydraulic system is filled. The venous line section of the system first remains open to the atmosphere or is connected to a drain, a container or a bag so that air inside the system can escape/be vented in the atmosphere. As soon as the filling process is completed, the venous line section is connected to the second fluid connector of the bag in order to circulate the fluid inside the hydraulic system of the extracorporeal blood treatment device for a certain period of time or a certain volume of flow through the bag chamber.

During this optional circulation process, the fluid flows through internal filtering devices in which remaining air pockets are removed/filtered out with the fluid. If necessary, the venous line section of the hydraulic system can again be disconnected from the second fluid connector of the fluid bag and the fluid inside the hydraulic system can be flushed out again under constant supply of fluid from the container.

Upon termination of the circulation process, the filling/circulation cycle preparing for patient treatment is completed so that the two line sections (venous and arterial) can be disconnected from the fluid bag and connected up to the patient for treatment.

The description above of the filling/circulation cycle of a hydraulic system/fluid conducting system of an extracorporeal blood treatment device (dialysis machine) known from the state of the art indicates that the fluid bag remains in the system circuit for the filling and circulation processes, i.e. that the fluid inside the system is circulated through the fluid bag and/or its fluid chamber. As a result, the fluid in the fluid bag may get contaminated. The consequence of this is that with each new treatment preparation of the extracorporeal blood treatment device, a new fluid bag with fresh, uncontaminated fluid is used for the following filling/circulation cycle, whereas the fluid bag for the filling/circulation cycle performed before is disposed of independently of its residual content. It is obvious that this procedure results in the wasting of a large quantity of fluid in case of a high patient treatment number because the fluid content of a fluid bag can only be used (incompletely) for one filling/circulation cycle.

Furthermore, the fluid bags for blood treatment devices effectively concern a custom-made design with two separate fluid connectors, as a result of which manufacturing becomes more expensive due to smaller numbers as compared with conventional NaCl bags/bottles on the whole.

SUMMARY OF THE INVENTION

In view of these problems, the task of the invention in hand is to provide a filling device of a fluid system of this kind, preferably an extracorporeal blood treatment device, and a filling procedure which can be operated more efficiently and thus more cost-efficiently as compared to the state of the art. Furthermore, a purpose of the invention in hand is to make available a fluid system equipped with the filling device according to aspects of the invention, for example, an extracorporeal blood treatment device, that can be operated in a simple manner and that enables the use of conventional fluid bottles (e.g. NaCl bottles).

This task is completed with a filling device of a fluid system/liquid system means for filling a fluid system, preferably an extracorporeal blood treatment device (dialysis, apheresis machine) with the characteristics of the independent claim. Furthermore the further goal is achieved with a fluid conducting system (means for conducting fluid). Furthermore the task is achieved with a procedure with the characteristics of claim 15 and/or 16. Advantageous embodiments of the invention are the object of sub-claims.

The basic idea of the invention in hand is to design the class-specific filling device of a fluid conducting system, in particular an extracorporeal blood treatment system, in such a way that a conventional (price-effective) fluid container (means for storing fluid) of a known design such as a conventional NaCl bottle or a suitable bag with a single puncturable/connectable connector can be used. Furthermore, the filling device according to aspects of the invention has, as a central component, a so-called spike (means for connecting a fluid containing puncturing) for connecting up the single fluid connector of a conventional medical fluid container (e.g. NaCl bottle), to which the manually operable fluid blocking mechanism (means for blocking a fluid flow), for example a stop valve, is connected downstream, which is adapted or designed in such a way so as to remain constantly fluidically connected with the spike. The fluid blocking mechanism has at least one fluid outlet connector which is adapted so that a line section/hose of a fluid conducting system/fluid system, preferably the arterial line section of a blood purification device/dialysis machine, can be connected to it in a detachable manner.

As a result of the arrangement of the fluid blocking mechanism on the spike, the spike can remain on the conventional medical fluid container after puncturing of the container seal, whereas the arterial line section can optionally be connected to the fluid blocking mechanism for a filling process of the fluid conducting system and then be disconnected again from the fluid blocking mechanism without losing any fluid from the medical fluid container. As the arterial line section is disconnected from the outlet connector of the fluid blocking mechanism (e.g. Luer-Lock fitting), the arterial line section can be reconnected to an arterial patient access immediately afterwards without any changes having to be performed on the arterial line section and/or its connector. This simplifies the handling of the filling device.

Preferably, the fluid blocking mechanism is a 3-way switch, for example a Y- or T-piece or a 3-way valve, whereby the conduits/connectors can optionally be shut off manually—(for example with clamps on the conduits/connectors or with the valve) in order to close off the switch completely and/or to fluidically connect the conduits optionally and/or to allow a fluid flow at least between two selected conduits. According to aspects of the invention, the 3-way switch, preferably the 3-way valve, is arranged directly downstream of this one, preferably universal medical fluid container. In the specific case, a first connector of the 3-way switch (of the 3-way valve) is coupled with the so-called spike (or another different connecting device) or is (integrally) designed with it, with which a fluid chamber of the fluid container can be tapped. To a second connector of the 3-way switch (of the 3-way valve), the arterial line section, and to a third connector of the 3-way switch (of the 3-way valve), a venous line section of the fluid system can be connected. Furthermore, the 3-way switch, preferably the 3-way valve, can preferably be put and/or switched manually in at least three positions, of which in a first switch position, the first connector is exclusively fluidically connected with the second connector and/or a fluid flow between these two connectors is possible and the third connector is closed (single-pass switch position), in a second switch position, the second connector is fluidically connected with the third connector and/or a fluid flow between these two connectors is possible and the first connector is closed (circulation switch position), and in a third switch position, all three connectors are disconnected from each other and/or closed.

A medical fluid/liquid system equipped in such a way enables the coupling of the conventional fluid container with the arterial line section for the filling process (with the venous line section disconnected) by putting the 3-way switch, preferably the 3-way valve, in the first switch position, and connecting the arterial line section with the venous line section for the circulation process by putting the 3-way switch, preferably the 3-way valve, in the second switch position. As the first connector of the 3-way switch, preferably the 3-way valve, is closed in this second switch position, the fluid container is disconnected from the hydraulic system/circuit of the extracorporeal blood treatment device so the remaining fluid in it is not contaminated by the fluid circulating in the hydraulic system. As in the third switch position of the 3-way switch, preferably the 3-way valve, all of its connectors are closed, the two line sections of the hydraulic system can be disconnected in this switch position and connected to the patient for treatment.

As a result, the fluid container can be used for several subsequent treatments depending on the fill volume so that no fluid is lost any more. Furthermore, the medical filling device for a conventional/universal medical fluid container is provided, which is more cost-efficient in comparison with the specially designed containers with two connectors for extracorporeal blood treatment devices. Finally, the fluid container used does not require any connector, in particular for the case that the so-called spike is connected to the 3-way switch, preferably the 3-way valve, or is combined with it into an integral modular unit. In the latter case, the spike can be connected effectively transition-free, i.e. without interposition of a (bridging) pipe section, directly with, the first connector, preferably in one piece or screwed on it.

The medical fluid system/fluid conducting system according to aspects of the invention, preferably a blood purification system (dialysis machine), has a filling device according to the design described above and a venous line section and an arterial line section, of which at least the arterial line section is adapted in such a way that it is or can be optionally connected to the filling device. Furthermore, at least the arterial line section has, directly downstream of its connector interacting with the filling device, (a component) a blocking mechanism (e.g. a hose clamp as further component) with which the arterial line section can be temporarily fluidically closed for reconnecting from the filling device to an arterial patient access and vice versa. Preferably the venous line section has the same components as the arterial line section.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

According to FIG. 1, an extracorporeal blood treatment device 1, preferably a dialysis or apheresis machine, has an internal hydraulic conducting system (hereinafter referred to as fluid conducting system) through which during a treatment phase on the machine side, for example, a blood purification fluid (dialysis fluid) is passed, and on the patient side, blood flows through it extracorporeally, whereby the machine-side and the patient-side fluid conducting systems are fluidically separated in case of a dialysis machine by a dialyser (filter) that is not shown in more detail. For this purpose, the fluid conducting system has a venous line section and an arterial line section 2, 4 on the patient side, preferably with connectors (Luer-Lock fittings) 6, 8 on each hose section arranged/formed on the ends in each case to which, for example, injection needles or cannulas (not depicted) can be connected as patient access, which can be introduced in a patient's body.

In order to avoid a possibly necessary washing out of possible contaminations resulting from manufacturing in the patient's body, the extracorporeal blood treatment device 1 has a filling device which enables a circulation process (consequently hereinafter referred to as circulation device) with which the fluid conducting system is cleaned as a rule before every patient treatment.

Figure 1:
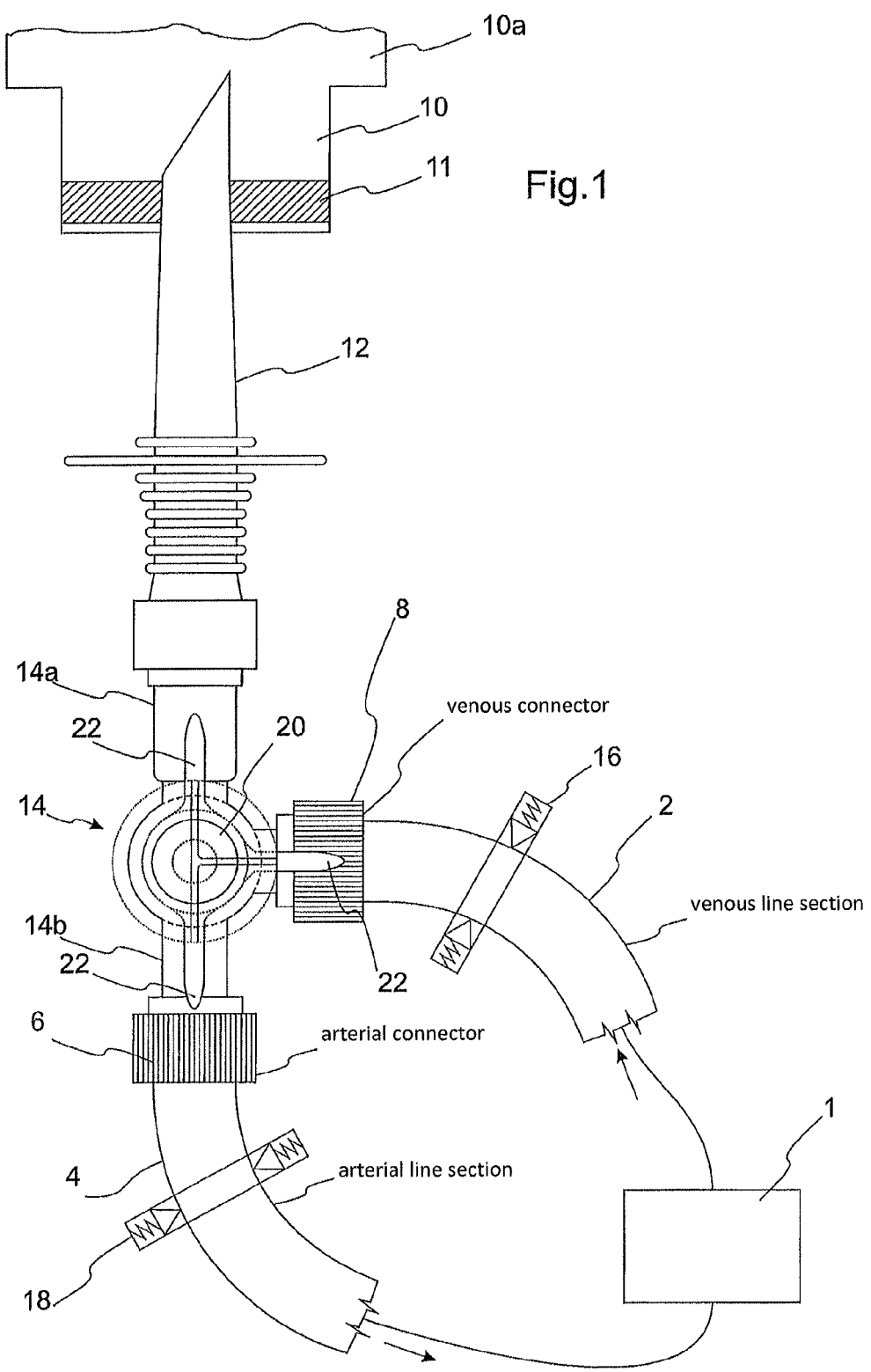
FIG. 1 shows a fluid system, preferably in the form of a circulation device of an extracorporeal blood treatment device, according to a preferred exemplary embodiment of the invention.

According to FIG. 1, the filling/circulation device according to aspects of the invention in hand has a fluid source in the form of a universal fluid container (NaCl bottle) 10 with a single outlet 11, which is punctured in the exemplary embodiment in hand with a spike 12 of the filling device in order to tap fluid from the fluid container 10. The design of the spike 12 matches known spike structures so that its design does not have to be explained in more detail here. Furthermore, it is to be pointed out that, for example, in case of a Luer-Lock or another fitting on the container side, the spike may replaced by a suitable connecting piece on the side of the filling/circulation device.

Furthermore, the filling/circulation device according to aspects of the invention has a fluid blocking mechanism in the shape of a 3-way switch, preferably a 3-way valve 14, which is arranged directly downstream of the spike 12 (connecting piece) in the direction of flow away from the fluid container 10. In the case in hand, the spike 12 is directly (without interposition of an additional line section) connected to the 3-way valve 14. As an alternative, the spike 12 can also be realised in one piece or as a modular unit with the 3-way valve 14.

For that purpose, the 3-way valve 14 has a first connector or fluid inlet 14a that is fluidically connected with the spike 12 and/or to which the the fluid source 10 can be connected/is connected. Furthermore, the 3-way valve 14 has a second connector 14b, to which the arterial line section 4 of the patient-side fluid conducting system of the extracorporeal blood treatment device 1 can be connected. Finally, the 3-way valve 14 has a third connector 14c, to which the venous line section 2 of the patient-side fluid conducting system of the extracorporeal blood treatment device 1 can be connected. The venous line section as well as the arterial line section 2, 4 are each equipped with a hose clamp 16, 18 or a similar blocking mechanism in order to close the respective hose section temporarily as an option.

The 3-way valve 14 in hand has a manually operable rotary lock consisting of a rotating cylindrical valve piston 20 that is equipped/designed on the front side with a handle, preferably in the shape of (three) intervention vanes 22. The valve piston has a central longitudinal bore, of which three radial bores branch off at equal distances in circumferential direction. The intervention vanes 22 are arranged in such a way that they are aligned along the radial bores and so indicate the flow direction of the radial bores. Such a 3-way valve is sufficiently known from the state of the art so that a further description, in particular of its function, can be dispensed with here.

FIG. 2 to 5 show the switch positions intended according to aspects of the invention of the 3-way valve 14 in dependence on the current operating phases of the extracorporeal blood treatment device 1, which are described below in connection with the functions intended to be performed with it.

Figure 2:
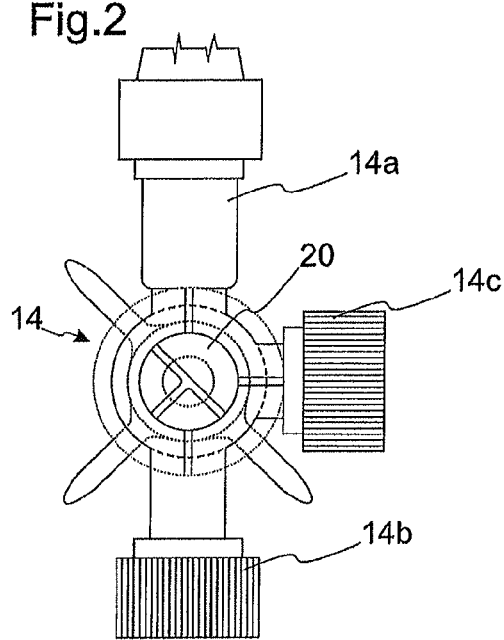
FIG. 2 shows a closed switch position of a filling device in the form of a 3-way valve of the circulation device according to FIG. 1 as a possible variant of the filling device according to aspects of the invention (here 3-way switch), whereby it is already pointed out here that, for example, a Y- or T-piece with hose blocking mechanism (hose clamps) can also be provided on each branch conduit upstream of the internal filling device connectors.

According to FIG. 2, the 3-way valve 14 is shown in a shut-off position in which all three connectors 14a-14c are closed. In this switch position, spike 12 can puncture the outlet 12 of the universal fluid container 10 and so tap the fluid stored in there (in the chamber 10a formed by the container) without losing fluid into the atmosphere.

Figure 3:
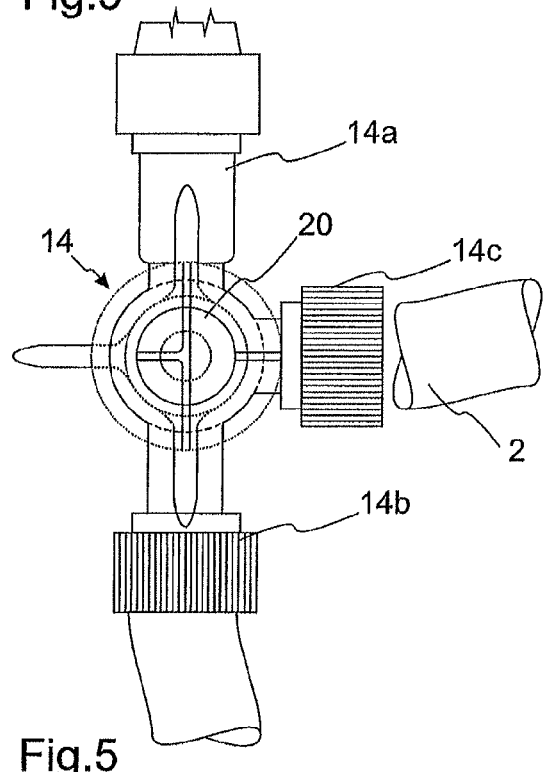
FIG. 3 shows a "single-pass" switch position of the 3-way valve of the circulation device according to FIG. 1, in which a fluid source (fluid container) is exclusively fluidically connected with an arterial line section of the extracorporeal blood treatment device.

FIG. 3 shows the so-called "single-pass" switch position in which the first connector 14a is fluidically connected with the second connector 14b, while the third connector 14c is closed. In this switch position, the arterial line section 4 is already connected to the second connector 14b, but the venous line section 2 is open to the atmosphere or connected to a drain/receiver tank.

In this switch position, fluid (NaCl solution) from the conventional fluid container with a single connector is passed through the 3-way valve 14 in the arterial line section and so the patient-side fluid conducting system is flooded constantly until the fluid runs out of the venous line section 2. This means that the venous line section 2 serves as air vent during this system filling process. It has to be pointed out that the hose clamps 16, 18 are naturally open during this process.

Figure 4:
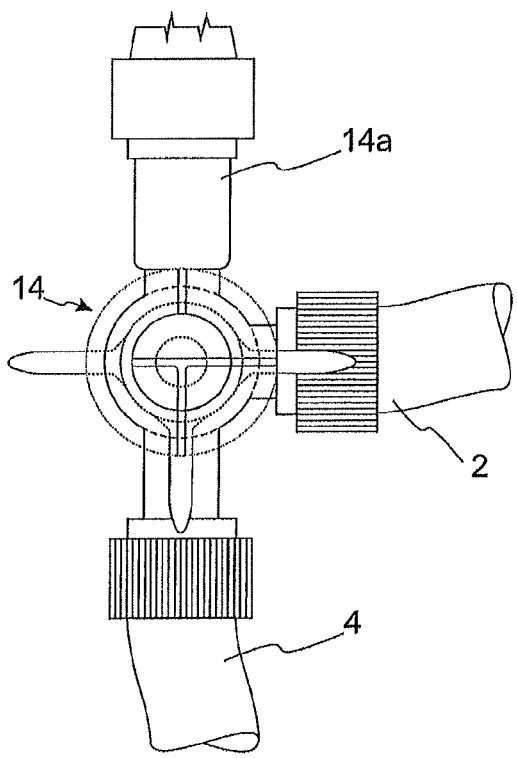
FIG. 4 shows a "circulation" switch position of the 3-way valve of the circulation device according to FIG. 1, in which the arterial line section is exclusively fluidically connected (short-circuited) with a venous line section of the extracorporeal blood treatment device and the fluid source is fluidically separated from the extracorporeal blood treatment device.
Figure 5:
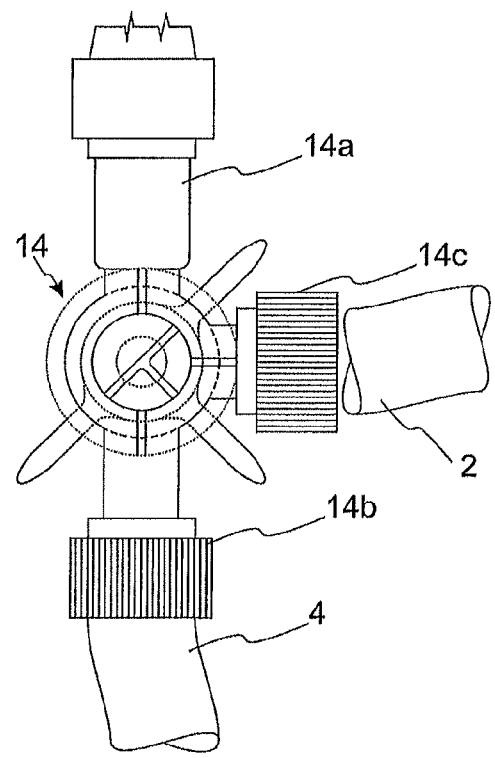
FIG. 5 shows another closed switch position of a 3-way valve of the circulation device according to FIG. 1.

As soon as the system has been filled with fluid from the fluid container 10, the venous line section is connected to the third connector 14c of the 3-way valve 14, and the 3-way valve 14 is put in the switch position according to FIG. 4, which can be referred to as "circulation" switch position. In this switch position, the second and third connectors 14b, 14c of the 3-way valve 14 are fluidically connected with each other, while the first connector 14a is closed.

If now the fluid contained in the fluid conducting system is circulated, it flows, starting from the venous line section 2, through the 3-way valve 14, and from there, is again passed on in the arterial line section 4 without fluid being able to enter the fluid container 10. Consequently, the fluid stored in there remains uncontaminated.

After a predetermined time of circulation, the 3-way valve 14 is put in the switch position shown in FIG. 5, in which again all three connectors 14a-14c are closed. You can see that the switch position according to FIG. 5 differs from the switch position according to FIG. 2 because the valve piston 20 was not simply turned back all the way in the first shut-off position according to FIG. 2, but was turned back in the second shut-off position according to FIG. 5, which is consequently diametrically opposite the first shut-off position. If the valve piston 20 had been turned back all the way, it would at least temporarily have passed through the "single pass" position, in which contaminated fluid from the fluid conducting system could possibly have penetrated the fluid container.

As soon as the 3-way valve 14 is closed, the venous line section 2 is now again disconnected from the 3-way valve 14 and the valve piston 20 is turned in the "single-pass"

position according to FIG. 3 in order to flush the contaminated fluid from the fluid conducting system. Upon completion of this process, the filling/circulation cycle is completed.

Then the 3-way valve 14 is closed again, all hose clamps 16, 18 downstream of the 3-way valve 14 are put in the shut-off position, and the arterial line section is also disconnected from the 3-way valve 14 so that it can be connected together with the venous line section to the patient's body.

Here it has to be pointed out that according to the description in hand, the filling device according to aspects of the invention is designed with the 3-way switch as a fluid blocking mechanism so that a circulation mode can be performed. However, it is also conceivable to design the blocking mechanism according to aspects of the invention as a simple closing valve with an inlet connector and an outlet connector, which then allows only a "single-pass mode" according to the definition above. In every case, the filling device according to aspects of the invention in hand allows a preferably manual shutting off of the spike outlet so that the spike can remain in the fluid container upon completion of the "single-pass mode" and at least the arterial line section disconnected from it can be connected up with its internal connector to the patient access that was already established without further measures having to be taken.

Furthermore, it is conceivable to provide another (or alternatively to the fully closed switch position) switch position for the 3-way switch in which all three conduits are open and thus fluidically connected with each other. This position is technically relevant if sterile products are used, for example.

In summary, the invention in hand concerns a filling device, for example in the form of a circulation device, of an extracorporeal blood treatment device 1 with a preferably universal medical fluid container 10 to which an arterial line section 4 of a fluid conducting system of the extracorporeal blood treatment device 1 can be connected as an option. Furthermore, the filling device has a spike as well as a fluid blocking mechanism, for example a 3-way switch, preferably a 3-way valve, which is arranged directly downstream of the spike 12. A conduit 14a of the 3-way switch is coupled with the spike 12 or a similar connecting device or is formed in one piece together with it.

The invention claimed is:

1. Method for performing a filling and recirculation process of a blood-side conducting system of a dialysis machine using a filling device including a spike configured for connecting to a single fluid connector of a medical fluid container of a fluid system and a 3-way switch arranged downstream of the spike that is configured to remain fluidly connected with the spike while the filling device is in operation, wherein the 3-way switch has a second conduit that is adapted such that an arterial line section of the blood side conducting system can be detachably connected while the filling device is in operation, wherein the method comprises the steps of:
   a. connecting the spike to the single fluid connector of the medical fluid container with the 3-way switch completely closed and connecting the arterial line section to the second conduit of the closed 3-way switch with a venous fluid line section of the blood side conducting system open to the environment;
   b. flushing a fluid flow path extending along the arterial line section and the venous fluid line section by fluidly connecting the spike with the second conduit of the 3-way switch;
   c. completely closing the 3-way switch and connecting the venous fluid line section to a third conduit of the 3-way switch;
   d. recirculating filled-in fluid in the fluid flow path by short-circuiting the second and third conduits on the 3-way switch and simultaneously closing off the spike;
   e. completely closing the 3-way switch and uncoupling the venous fluid line section from the third conduit and repeatedly flushing the fluid flow path according to step b.; and
   f. completely closing the 3-way switch in preparation for the subsequent connection of the arterial and venous fluid line sections to a patient.

2. Method for performing the filling and recirculation process of the blood-side conducting system of the dialysis machine according to claim 1, wherein a first conduit of the 3-way switch is a fluid inlet that is coupled with the spike or is integrated into the spike, the second conduit of the 3-way switch is coupled to the arterial line section, and a third conduit of the 3-way switch is coupled to the venous line section.

3. Method for performing the filling and recirculation process of the blood-side conducting system of the dialysis machine according to claim 2, wherein the 3-way switch has at least three positions including a first switch position in which the first conduit is fluidly connected with the second conduit to allow fluid flow in between and the third conduit is closed, a second switch position in which the second conduit is fluidly connected with the third conduit to allow fluid flow in between and the first conduit is closed, and a third switch position in which all three conduits are closed.

4. Method for performing the filling and recirculation process of the blood-side conducting system of the dialysis machine according to claim 3, wherein the 3-way switch is a 3-way valve that can be activated manually and wherein the 3-way valve includes a rotary piston and a handle for manual activation of the 3-way valve.

5. Method for performing the filling and recirculation process of the blood-side conducting system of the dialysis machine according to claim 3, wherein the fluid container for the filling process is coupled with the arterial line section using a single-pass principle by placing the 3-way switch in the first switch position, the arterial line section is connected with the venous line section for the circulation process by placing the 3-way switch in the second switch position, and the first conduit of the 3-way switch is closed to fluidly separate the fluid container from the fluid conducting system of the extracorporeal blood treatment device in the second switch position.

6. Method for performing the filling and recirculation process of the blood-side conducting system of the dialysis machine according to claim 5, wherein in the third switch position of the 3-way switch all conduits of the 3-way switch are closed such that the arterial and venous line sections of the fluid conducting system can be disconnected from the fluid container.

7. Method for performing the filling and recirculation process of the blood-side conducting system of the dialysis machine according to claim 1, wherein the spike is connected to the 3-way switch with a Luer-Lock fitting.

8. Method for performing the filling and recirculation process of the blood-side conducting system of the dialysis machine according to claim 1, wherein the spike is integrated with 3-way switch as an integral modular unit.

9. Method for performing the filling and recirculation process of the blood-side conducting system of the dialysis machine according to claim 1, wherein the spike is connected directly to the 3-way switch transition-free without interposition of a bridging line section.

* * * * *